(12) United States Patent
Ayliffe

(10) Patent No.: US 8,804,105 B2
(45) Date of Patent: Aug. 12, 2014

(54) COMBINED OPTICAL IMAGING AND ELECTRICAL DETECTION TO CHARACTERIZE PARTICLES CARRIED IN A FLUID

(75) Inventor: Harold E. Ayliffe, Hailey, ID (US)

(73) Assignee: E. I. Spectra, LLC, Hailey, ID (US)

( * ) Notice: Subject to any disclaimer, the term of this patent is extended or adjusted under 35 U.S.C. 154(b) by 175 days.

(21) Appl. No.: 13/431,877

(22) Filed: Mar. 27, 2012

(65) Prior Publication Data

US 2013/0258318 A1 Oct. 3, 2013

(51) Int. Cl.
*G01N 21/00* (2006.01)

(52) U.S. Cl.
USPC .......................................................... 356/72

(58) Field of Classification Search
USPC .......................................................... 356/72
See application file for complete search history.

(56) References Cited

U.S. PATENT DOCUMENTS

| | | |
|---|---|---|
| 2,656,508 A | 10/1953 | Colter |
| 3,910,702 A | 10/1975 | Corll |
| 4,130,754 A | 12/1978 | Fosslien |
| 4,164,870 A | 8/1979 | Scordato et al. |
| 4,488,814 A | 12/1984 | Johnson |
| 4,873,875 A | 10/1989 | Cork |
| 5,126,022 A | 6/1992 | Soane et al. |
| 5,338,427 A | 8/1994 | Shartle et al. |
| 5,376,878 A | 12/1994 | Fisher |
| 5,459,406 A | 10/1995 | Louge |
| 5,516,564 A | 5/1996 | Root et al. |
| 5,695,092 A | 12/1997 | Schrandt |
| 5,800,690 A | 9/1998 | Chow et al. |
| 5,933,707 A | 8/1999 | Ayliffe et al. |
| 6,045,676 A | 4/2000 | Mathies et al. |
| 6,091,975 A | 7/2000 | Daddona et al. |
| 6,169,394 B1 | 1/2001 | Frazier et al. |
| 6,285,807 B1 | 9/2001 | Walt et al. |
| 6,382,228 B1 | 5/2002 | Cabuz et al. |
| 6,396,584 B1 | 5/2002 | Taguchi et al. |
| 6,426,615 B1 | 7/2002 | Mehta |
| 6,437,551 B1 | 8/2002 | Krulevitch et al. |
| 6,440,725 B1 | 8/2002 | Pourahmadi et al. |
| 6,454,945 B1 | 9/2002 | Weigl et al. |
| 6,488,896 B2 | 12/2002 | Weigl et al. |
| 6,638,482 B1 | 10/2003 | Ackley et al. |
| 6,656,431 B2 | 12/2003 | Holl et al. |
| 6,663,353 B2 | 12/2003 | Lipscomb et al. |
| 6,674,525 B2 | 1/2004 | Bardell et al. |
| 6,703,819 B2 | 3/2004 | Gascoyne et al. |
| 6,794,877 B2 | 9/2004 | Blomberg et al. |
| 7,204,139 B2 | 4/2007 | Takayama |
| 7,223,363 B2 | 5/2007 | McNeely et al. |
| 7,223,371 B2 | 5/2007 | Hayenga et al. |
| 7,235,400 B2 | 6/2007 | Adey |
| 7,332,902 B1 | 2/2008 | Vermiere et al. |

(Continued)

*Primary Examiner* — Tarifur Chowdhury
*Assistant Examiner* — Omar Nixon
(74) *Attorney, Agent, or Firm* — Brian C. Trask

(57) ABSTRACT

An apparatus for, and a method of, characterizing a plurality of particles carried by a fluid that can be urged to move through a channel in a microfluidic cassette by combining data analysis of a first signal that is optically-based, and data analysis of a second signal that is electrically-based. Optically-based information is typically obtained by a digital image sensor. Electrically-based information can be obtained by direct measurement of impedance; sometimes in an arrangement operating under the Coulter principle. Data provided by exemplary characterization includes at least one of: volumetric cell count; viability percentage or ratio; particle type; and a particle size histogram.

19 Claims, 13 Drawing Sheets

(56) References Cited

U.S. PATENT DOCUMENTS

| | | |
|---|---|---|
| 7,392,908 B2 | 7/2008 | Frazier |
| 7,410,809 B2 | 8/2008 | Goix et al. |
| 7,417,418 B1 | 8/2008 | Ayliffe |
| 7,515,268 B1 | 4/2009 | Ayliffe et al. |
| 7,520,164 B1 | 4/2009 | Ayliffe |
| 7,579,823 B1 | 8/2009 | Ayliffe |
| 2002/0061260 A1 | 5/2002 | Husar |
| 2002/0117517 A1 | 8/2002 | Unger et al. |
| 2002/0149766 A1 | 10/2002 | Bardell et al. |
| 2003/0180965 A1 | 9/2003 | Yobas et al. |
| 2004/0037739 A1 | 2/2004 | McNeely et al. |
| 2004/0151629 A1 | 8/2004 | Pease et al. |
| 2005/0054078 A1 | 3/2005 | Miller et al. |
| 2005/0118705 A1 | 6/2005 | Rabbitt et al. |
| 2005/0255600 A1 | 11/2005 | Padmanabhan et al. |
| 2006/0073609 A1 | 4/2006 | Shimizu |
| 2007/0292941 A1* | 12/2007 | Handique et al. .......... 435/288.7 |
| 2010/0255473 A1* | 10/2010 | Ermantraut et al. .............. 435/6 |

\* cited by examiner

COMBINED OPTICAL IMAGING AND ELECTRICAL DETECTION TO CHARACTERIZE PARTICLES CARRIED IN A FLUID

BACKGROUND

1. Field of the Invention

This invention relates to characterization of particles entrained in a fluid carrier medium. It is particularly directed to a combination of optically-based characterization of particles and electrically-based detection of a fluid boundary and/or one or more particles.

2. State of the Art

Optically-based data acquisition has been in existence for a very long time. Exemplary such optically-based data acquisition includes a human examining stained slides under a microscope, and counting particles (e.g. cells) contained on the slide. Such work is tedious, and errors are difficult to avoid. Computerized digital image evaluation has been developed to avoid some of the difficulties associated with manual optical data collection.

Electrically-based data acquisition of particles entrained in a fluid carrier has also been in existence for a very long time. Pioneering work in particle detection by measuring impedance deviation caused by particles flowing through a small aperture between two containers of electrically conductive fluid is disclosed in U.S. Pat. No. 2,656,508 to W. H, Coulter. Coulter's name is now associated with the principle of particles causing a change in electric impedance as they occlude a portion of the aperture. Since publication of his patent, considerable effort has been devoted to developing and refining sensing devices operating under the Coulter principle. Relevant US patents include U.S. Pat. No. 5,376,878 to Fisher, U.S. Pat. No. 6,703,819 to Gascoyne et al., U.S. Pat. No. 6,437,551 to Krulevitch et al., U.S. Pat. No. 6,426,615 to Mehta, U.S. Pat. No. 6,169,394 to Frazier et al., U.S. Pat. No. 6,454,945 and U.S. Pat. No. 6,488,896 to Weigl et al., U.S. Pat. No. 6,656,431 to Holl et al., and U.S. Pat. No. 6,794,877 to Blomberg et al. Patent application 2002/117,517 to Unger et al. is also relevant. Each above-referenced document is hereby incorporated by reference, as though set forth herein in their entireties, for their disclosures of relevant technology and structure employed in various sensor arrangements.

BRIEF SUMMARY OF THE INVENTION

This invention provides an apparatus, and method for using such an apparatus, to combine optically-based data acquisition and electrically-based data acquisition to obtain information about particles carried in a fluid sample. Exemplary such information nonexclusively includes one or more of: particle count, volumetric particle count, viability data including ratio or percent, particle size(s), particle type(s), and the like.

An exemplary interrogation apparatus structured according to certain principles of the invention includes structure configured and arranged to interact with a removable microfluidic cassette to obtain an optically-based signal related to optical particle characterization of a plurality of particles carried by a fluid that can be urged to move through a channel in the cassette. The optically-based signal is typically extracted from an optical-interrogation location disposed along the channel in the cassette. The optical-interrogation location may be associated with a window that permits propagation of light energy, typically in a through-the-thickness direction, through the cassette. Preferred embodiments are essentially back-lit by light applied from one side of the cassette and detected on the other side of the cassette. However, it is within contemplation that certain embodiments may be top- or side-lit, and even that the cassette may, itself, include a light source.

The interrogation apparatus also includes structure configured and arranged to interact with the removable cassette to obtain an electrically-based signal related to at least one of: identification of the cassette; a location of a fluid boundary that can be urged to move through the channel; and characterization of one or more particles carried by sample fluid. Desirably, the interrogation apparatus also includes a display element on which a result from processing one or more of the optically-based signal and the electrically-based signal may be shown.

An exemplary removable microfluidic cassette is cooperatively structured to interface in operable registered reception inside an interrogation apparatus. Installation of such a cassette desirably places the cassette in-circuit with electrically-based interrogation circuitry carried by the interrogation apparatus. Electrically-based interrogation of sample fluid urged to flow through a cassette typically encompasses imposing an electric signal by the interrogation apparatus onto one or more electrically-conductive elements of the cassette. Such interrogation also includes monitoring, by the interrogation apparatus, an electrical signal between an electrode and ground, or cooperating electrodes carried in a channel in the cassette and disposed to contact sample fluid at discreet locations inside the channel. Among other uses, the monitored electrical signal can be used to determine a location of a fluid boundary, and/or to characterize particles in accordance with an adaptation of the Coulter principle.

Similarly, an installed cassette is desirably disposed in operable registration with optically-based interrogation structure carried by the interrogation apparatus. Exemplary optically-based interrogation structure may include a light source oriented to emit light energy to impinge through a sufficiently transparent window of a cassette, an optional focusing lens arrangement, and an image sensor oriented to receive the transmitted light, such as a CMOS chip. The light energy passing through the window is also directed through a portion of a channel in the cassette, where it illuminates particles (e.g. cells) in an optical interrogation location. Light energy captured by the image sensor can then be used to determine (e.g. count) the number of particles or cells in a given area corresponding to the optical interrogation location. Volumetric information corresponding to channel structure at the optical interrogation location can be used to determine volumetric particle count. Sometimes, a viability dye can be incorporated into sample fluid, and the resulting optically-based information obtained by the interrogation apparatus may include cell viability information, such as a live/dead ratio, or percent viability, and the like.

Typically, data desired by a user of the interrogation apparatus is displayed on a display element of the interrogation apparatus. Data may be displayed in any of conventional numeric, alphanumeric, or letter format, or graphically, or combinations thereof. One currently preferred data display, for certain types of test results, includes a histogram to indicate the number of particles detected in each of a plurality of discreet size-range groups. Of course, data obtained by an interrogation apparatus may be up-loaded in conventional fashion to a different device (such as a personal computer, mainframe, tablet, and the like) for further manipulation, display, and/or storage.

An exemplary method for using an apparatus structured according to certain principles of the invention includes: providing an interrogation apparatus structured according to certain principles of the invention; loading a cooperating removable microfluidic cassette into operable registration with respect to the interrogation apparatus; urging flow of a sample fluid through a channel disposed inside the cassette until a first electrically-based signal related to a first fluid boundary location in the channel is generated; and obtaining a first optically-based signal to permit determination of a first particle count related to the sample fluid.

BRIEF DESCRIPTION OF THE DRAWINGS

In the drawings, which illustrate what are currently considered to be the best modes for carrying out the invention.

DETAILED DESCRIPTION OF THE ILLUSTRATED EMBODIMENTS

Reference will now be made to the drawings in which the various elements of the illustrated embodiments will be given numerical designations and in which the invention will be discussed so as to enable one skilled in the art to make and use the invention. It is to be understood that the following description is only exemplary of the principles of the present invention, and should not be viewed as narrowing the claims which follow.

For purpose of this disclosure, a microfluidic cassette is defined as encompassing structures including channels with a thickness (or fluid depth) of less than about 2 mm. Channel widths of such devices may range up to about 6 mm. Devices structured according to certain principles of the instant invention encompass the micro to meso (meaning millimeter) range. The term "microfluidic" is used in this disclosure somewhat more broadly than might be its conventional definition. As used herein, the term "microfluidic" is intended to broadly encompass fluid flow arrangements that may urge particles of interest, which are carried by a fluid stream, into substantially single-file travel through an interrogation location. Exemplary devices to accomplish such behavior may contain a fluid flow constriction having a characteristic size on the order of between about a few microns to about millimeter scale, and sometimes, even larger.

For purpose of this disclosure, "characterization" nonexclusively encompasses detection of the presence (of something), qualification (e.g. size, type, viability, etc.), and quantification. Data provided by exemplary characterization includes at least one of: volumetric cell or particle count; viability percentage or ratio; particle type; and a particle size histogram.

Figure 1:
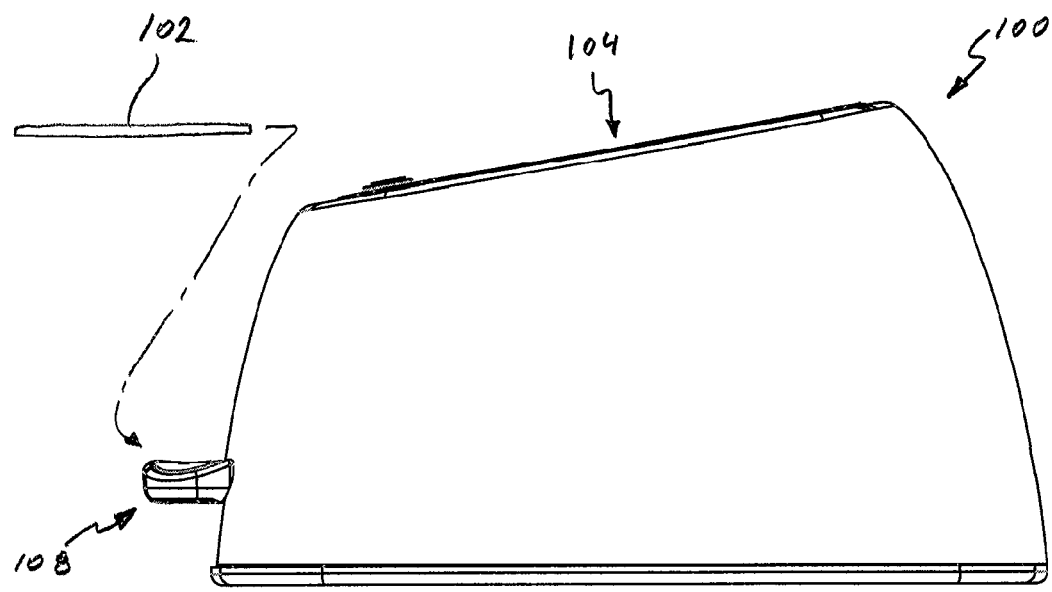
FIG. 1 is a side view of an interrogation apparatus structured according to certain principles of the invention.
Figure 2:
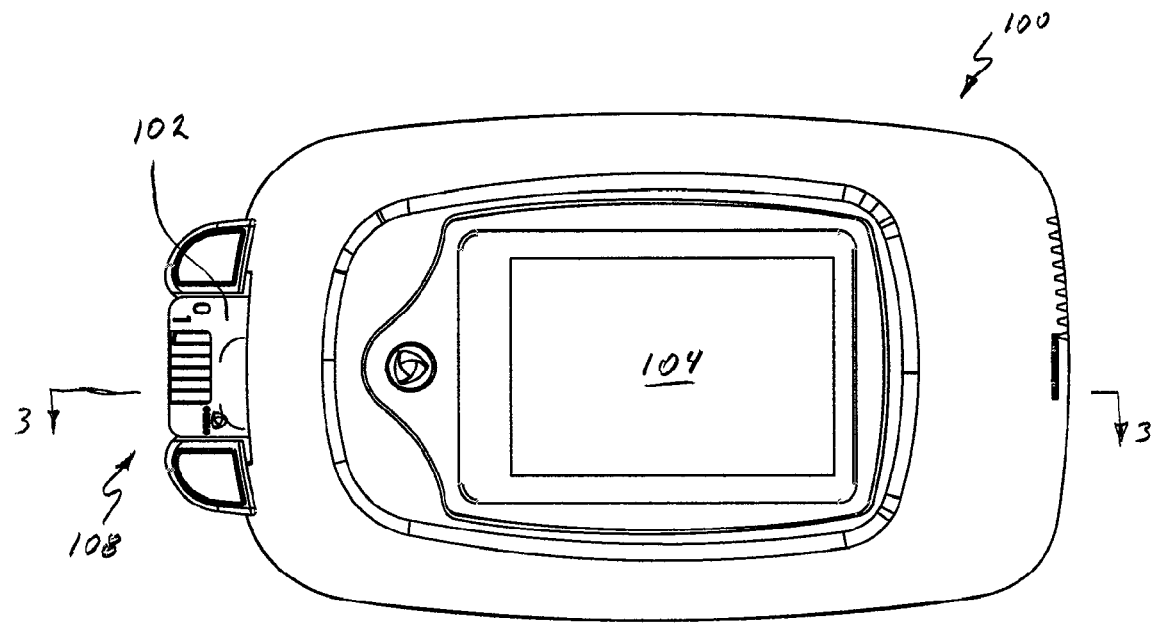
FIG. 2 is a top view of the device in FIG. 1.

A workable and exemplary interrogation apparatus structured according to certain principles of the invention is illustrated in FIGS. 1 and 2, and is generally indicated at 100. Interrogation apparatus 100 includes structure configured and arranged to interact with a removable microfluidic cassette 102 to obtain an optically-based signal related to optical particle characterization of a plurality of particles carried by a fluid that can be urged to move through a channel in the cassette 102. The optically-based signal is typically extracted from an optical-interrogation location disposed along the channel in the cassette. It is recognized that a fluid boundary location in a channel may also be determined by optically-based interrogation.

Interrogation apparatus 100 also includes structure configured and arranged to interact with the removable cassette 102 to obtain an electrically-based signal related to at least one of: identification of the cassette; a location of a fluid boundary that can be urged to move through the channel; and/or characterization of one or more particles carried by sample fluid. Desirably, the interrogation apparatus 100 also includes a display element 104 on which a result from processing one or more of the optically-based signal and the electrically-based signal may be shown.

As best shown in FIG. 1, a removable microfluidic cassette 102 is cooperatively structured for installation to interface in operable registered reception inside a cassette port, generally indicated at 108. Installation of a cassette 102 desirably places the cassette 102 in-circuit with electrically-based interrogation circuitry carried by the apparatus 100. Electrically-based interrogation of sample fluid urged to flow through a cassette 102 typically encompasses imposing an electric signal (e.g. time-varying, constant current, and the like) onto electrically-conductive elements of the cassette, and monitoring an electrical signal (e.g. impedance, differential voltage, and the like) between an electrode and ground or cooperating electrodes carried in a channel in the cassette 102 and disposed to contact sample fluid at discreet locations inside the channel. Among other uses, the monitored electrical signal can be used to determine a location of a fluid boundary, and/or to characterize particles in accordance with the Coulter principle.

Similarly, an installed cassette 102 is desirably disposed in operable registration with optically-based interrogation structure carried by the apparatus 100. Exemplary optically-based interrogation structure may include a light source oriented to emit light energy to impinge through a sufficiently transparent window of a cassette 102, an optional focusing lens arrangement, and an image sensor, such as a CMOS chip, oriented to receive the light transmitted through the window. The light energy passing through the window is also directed through a portion of a channel in the cassette, where it illuminates particle or cells in an optical interrogation location. Light energy captured by the image sensor can then be used to determine (e.g. count) the number of particles or cells in a given area corresponding to the optical interrogation location. Volumetric information corresponding to channel structure at the optical interrogation location (e.g. depth), and physical size of an image sensor (e.g. area), can be used to determine volumetric particle count. Sometimes, a viability dye (such as Trypan Blue) can be incorporated into sample fluid, and the resulting optically-based information obtained by the apparatus 100 may include cell viability information, such as live/dead cell counts, a live/dead ratio, or percent viability, and the like.

Typically, data desired by a user of the apparatus 100 is displayed on the display element 104. Data may be displayed in any of conventional numeric, alphanumeric, or letter format, or graphically, or combinations thereof. One currently preferred data display, for certain types of test results, includes a histogram to indicate the number of particles detected in each of a plurality of discreet size-range groups. One or more actual picture of the interrogated area (e.g. showing cell images) may be displayed. Of course, data obtained by apparatus 100 may be up-loaded in conventional fashion to a different device (such as a personal computer, mainframe, tablet, hand-held computing device, telephone, local area network, internet, and the like) for further manipulation, display, and/or storage.

Figure 3:
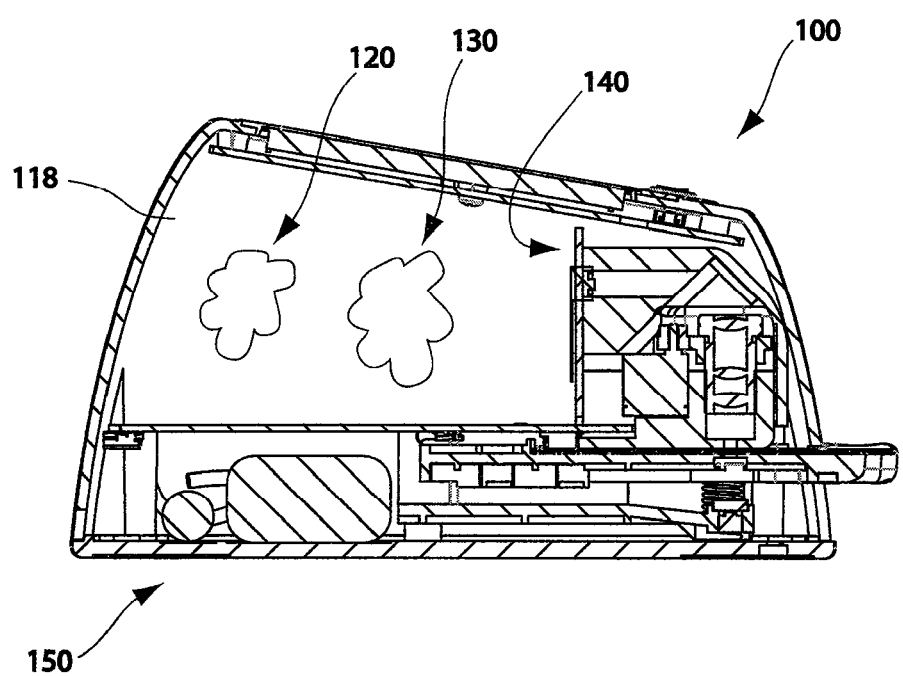
FIG. 3 is an illustrative cross-section view indicated at 3-3 in FIG. 2 and looking in the direction of the arrows.

As illustrated in FIG. 3, an exemplary interrogation apparatus 100 desirably includes structure arranged to define a plurality of subsystems. It has been found convenient to enclose various subsystems inside a housing 118. As illustrated, apparatus 100 includes structure, generally indicated at 120, defining a fluid motion-motivating system. An exemplary motion-motivating system includes a vacuum pump, and in certain cases, a vacuum reservoir. Advantageously, vacuum in a reservoir can be down-regulated and applied in a desired profile over time to a vent of a cassette to move sample fluid through the cassette.

Still with reference to FIG. 3, apparatus 100 also includes electrical interrogation structure, generally 130, and optical interrogation structure, generally 140. Exemplary such structures are detailed further, below. Some sort of structure to provide electrical power, generally 150, is also included, to operate apparatus 100. It is currently preferred for electrical power structure 150 to include an on-board battery, although electrical power may alternatively be provided in conventional fashion with a cord (not illustrated).

Figure 4:
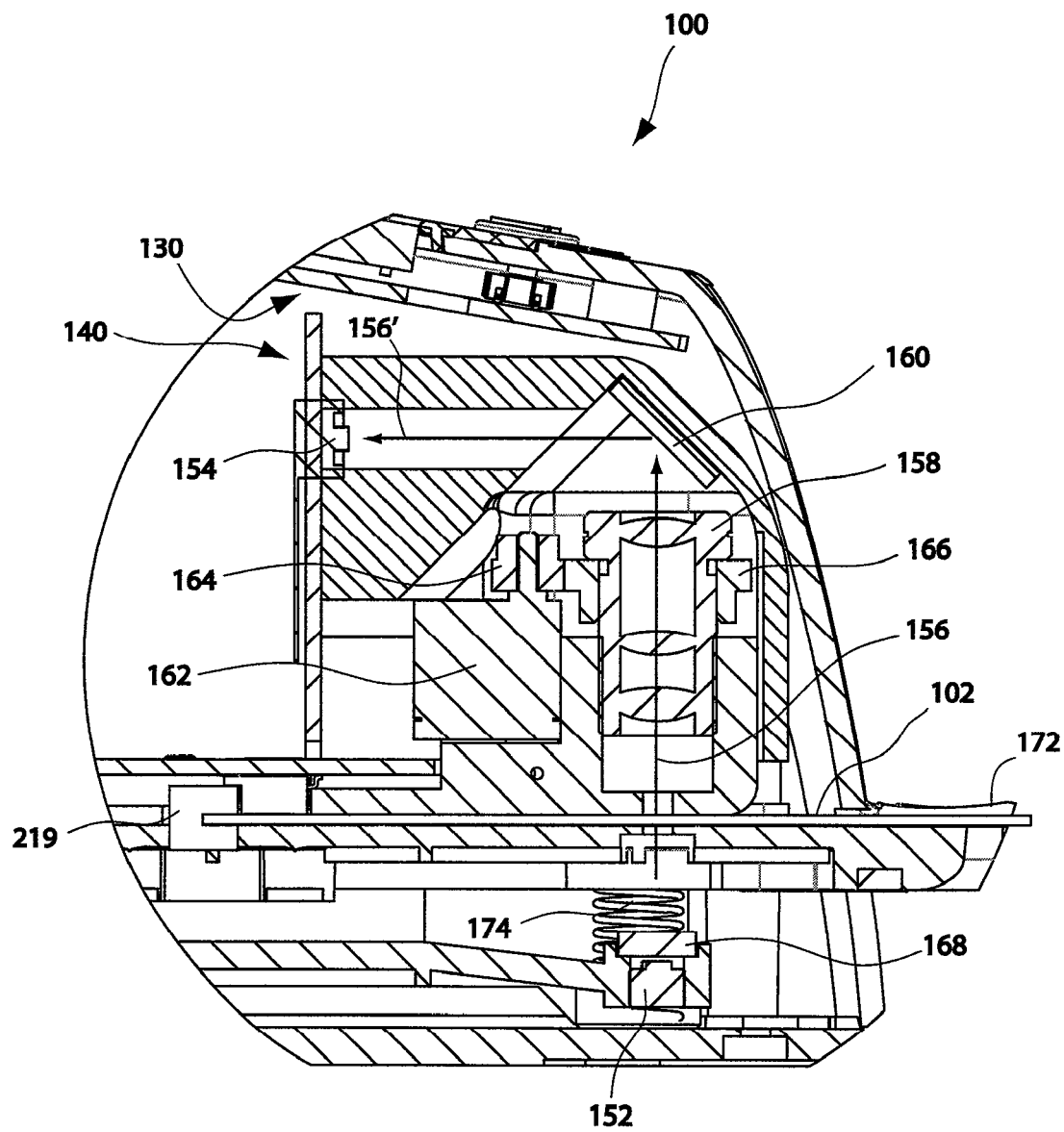
FIG. 4 is a close-up view illustrative of a workable cassette-loading portion of the cross-section illustrated in FIG. 3.

Exemplary optical interrogation structure 140 is illustrated in FIG. 4. One exemplary use of optical interrogation structure includes taking a picture of a large number of cells and then using image recognition software to determine what is a live cell and what is a dead cell (e.g. after Trypan Blue is added). The data is processed and a volumetric calculation is made to e.g. determine the actual volumetric cell concentration.

Optical interrogation structure 140 includes a light-emitting element, such as a light-emitting-diode (LED) 152 (or a laser, lamp, etc.), and a light recording element, such as image sensor 154. A workable image sensor 154 includes a CMOS device, although other sensors, such as CCD devices, and the like, are also workable. Light 156 emitted from LED 152 passes through the cassette 102 and a focusing lens arrangement 158 before being reflected by mirror 160 toward the image sensor 154. An operable focusing lens arrangement 158 may be selected to provide a magnification between about 1× to perhaps 10×, or so. The size of the optically-interrogated area is reduced in correspondence with increased magnification.

It is desirable to include an image sensor 154 that is capable of sufficient resolution. Pixel count per cell (or per cell diameter) is important. Pixel count is determined after the image is magnified by any intervening optic system. Typically, a minimum of about 8 pixels across the diameter of a cell is desirable. A workable CMOS sensor includes a rectangular array of 3264×2448 pixels. Such pixels in a preferred image sensor are about 1.4 µm×1.4 µm in size. One workable CMOS sensor includes model No. MT9E013, available on the world wide web at aptina.com.

Illustrated lens assembly 158 is a compound lens assembly that can be adjusted to focus light 156' reflected by minor 160 to impinge on image sensor 154. A motor 162 may be provided to adjust the focus of assembly 158. As illustrated, motor 162 is coupled through gear 164 and gear 166 to provide a focusing axial position adjustment of assembly 158. It is currently preferred to provide an automated focusing control that incorporates feedback from the image sensor 154. Sometimes, and as illustrated, a filter 168 may also be included in the optical path.

Still with reference to FIG. 4, it is currently preferred to provide an accurate and repeatable way to load a cassette in operable registration with respect to an interrogation apparatus, such as apparatus 100. A loading toggle lever 172 is provided in illustrated apparatus 100 to form an enlarged opening through which a cassette can be inserted. A spring 174 is disposed to urge the lever 172 and an installed cassette to a consistent loaded position. In the illustrated case, three sides of an installed cassette are used for purpose of enforcing a repeatable installed cassette location. Alternatively, a plurality of registration pins (not illustrated) may engage precision-located aperture(s) of a loaded cassette to enforce a consistent orientation between successive cassettes.

Figure 5:
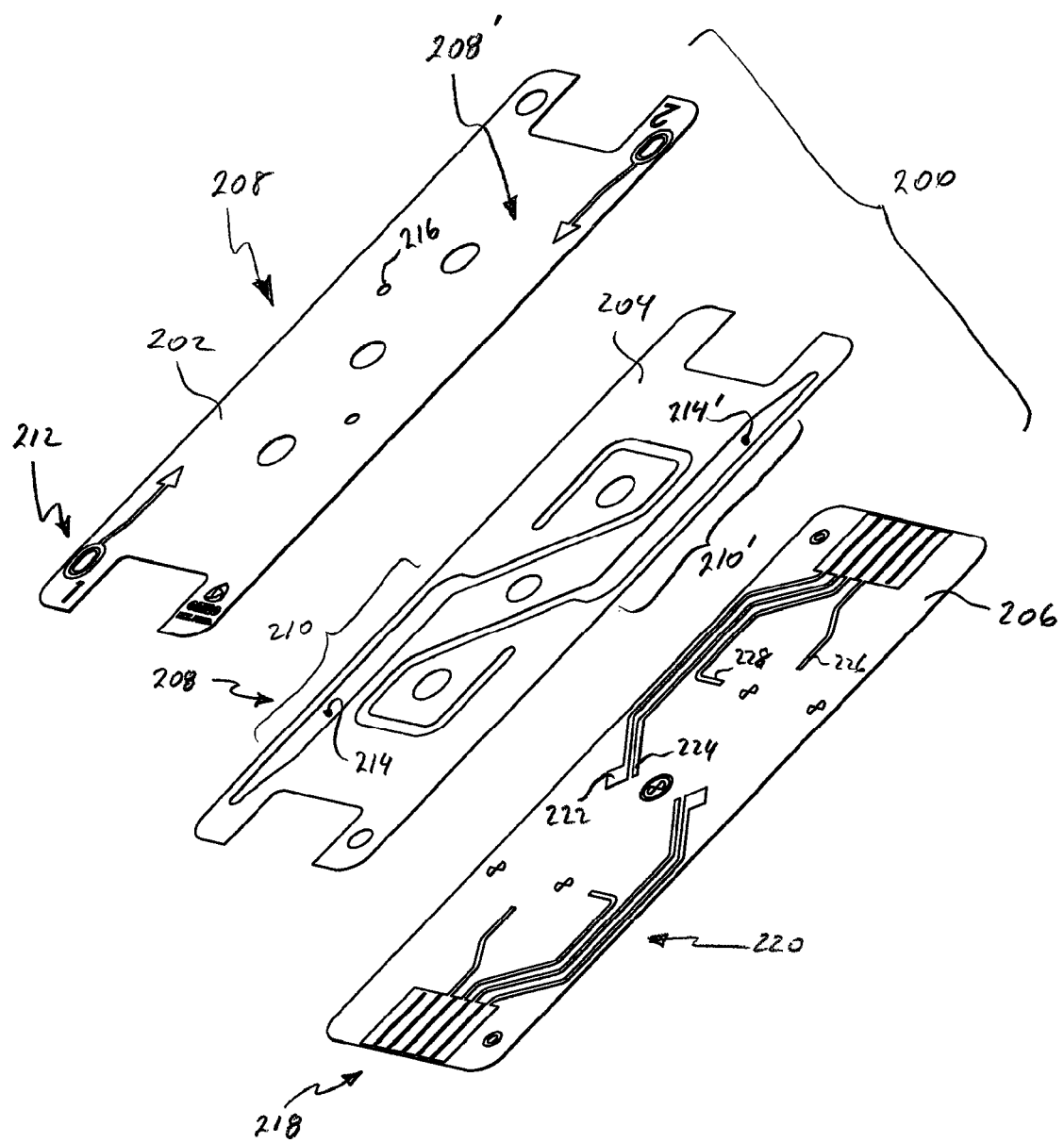
FIG. 5 is an exploded assembly view in perspective of a first preferred cassette.

A first exemplary cassette that can be used in accordance with certain principles of the invention is indicated generally at 200 in FIG. 5. Cassette 200 includes a plurality of thin film layers, including cap layer 202, channel layer 204, and interrogation layer 206. The currently preferred cap layer 202 and interrogation layer 206 are made from PET having a thickness of about 0.005 inches. Illustrated cassette 200 is a two-ended arrangement structured to provide duplicated structure forming first and second sensors on the same removable and reversible cassette 200. For clarity, the duplicated structures included in the illustrated second sensor are indicated with a prime.

The currently preferred channel layer 204 is made from double-sided adhesive film having a total thickness of about 0.0032 inches. Channel structure, generally indicated at 208, is provided by full-thickness cutouts made in the channel layer 204, and is patterned and arranged to provide fluid routing along a desired flow path. In an alternative embodiment within contemplation, a portion of channel structure may be essentially "carved out", embossed, "etched", or otherwise removed, from a portion of the thickness of a cap layer, such as layer 202. In any case, cassette 200 provides a window, generally indicated at 208, through which light e.g. 156, can pass through the cassette at an optical interrogation location, generally indicated at 210.

Cap layer 202 includes a sample aperture, or through-hole 212, disposed in fluid communication with optical interrogation channel 214. A vent aperture 216 is disposed in fluid communication with channel 214 at a downstream position. A reduced pressure (vacuum) can be applied to vent 216 to urge flow of a fluid sample from sample-receiving orifice 212 through the cassette 200.

It should be noted that this disclosure sometimes sets forth specific sizes for certain structure. Such is generally related to a preferred use of certain embodiments to interrogate blood samples. Therefore, for example, size of certain cassette structure is based upon interrogating particles having the approximate size of certain blood cells. Appropriate variation on size(s) will be apparent to one of skill in the art. For example, a desirable minimum channel height is related to particle size. Channel width in an optical interrogation location is typically selected to ensure proper fluid wetting. A general rule-of-thumb for channel width at an optical interrogation location is about ten-times the channel height.

Also, particles are assumed to have a characteristic "size", which may sometimes be referred to as a diameter, for convenience. However, it should be recognized that an interrogated particle may sometimes be formed as a combination of constituent particles, e.g. an analyte with one or more attached appropriately receptive bead. Certain preferred embodiments of the invention may be used to interrogate multi-sized populations of particles entrained in one or more fluid. Operable particles may include attached latex microspheres (beads), generally ranging in size from 0.5 μm to 35 μm in diameter, and this disclosure is structured accordingly. However, such is not intended to limit, in any way, the application of the invention to other fluids including fluids with particles having larger or smaller sizes.

A preferred channel for optical interrogation will provide a channel height of at least two-times the characteristic size (e.g. "diameter") of the particle to be interrogated. For the imaging cassette 200, a channel height of about 80 μm high channels is currently preferred. It is recognized that higher channels are better for conducting current in alternative cassettes that also operate on the Coulter principle, but higher channels are worse for imaging because they require either: 1) a larger depth of field of the lens; 2) longer settling times to allow the cells to sink down to the bottom channel surface; and/or 3) imaging at multiple heights to resolve cells throughout the channel thickness.

Interrogation layer 206 carries a plurality of electrically conductive elements that are patterned to form electrical contact pads, generally 218, and electrically conductive traces, generally 220. Contact pads 218 are adapted to facilitate connection of the cassette 200 to, and electrical communication with, an interrogation platform. A workable connection structure includes a single- or double-sided edge connector 219 (see FIG. 4) Conductive traces 220 are arranged to form surface electrodes disposed to contact sample fluid flowing at discreet locations along the fluid channel 214. An electrically-based signal (e.g. impedance, or voltage) measured between a driven electrode 222 and one of test electrodes 224, 226, or 228 (e.g. to ground) may be used to determine the locations of a fluid boundary as the sample fluid flows along channel 214. For example, prior to arrival of the electrolytic fluid, measured impedance at un-wetted electrodes will indicate an open-circuit. Desirably, a known channel volume is disposed between each of the test electrodes 224, 226, and 228 to permit determination of volumetric flow rate, sub-sample size, and the like.

The detected electrically-based signals obtainable from the illustrated embodiment 200 can be used, for non-limiting examples, to begin optically-based data collection at up to three times during a test; change a vacuum profile; and to terminate vacuum before undesirably drawing sample fluid through vent 216 and out of a cassette 200. Advantageously, optical image data can be averaged to increase accuracy of particle count in a sample fluid.

Certain of contact pads 218 may be configured to provide a continuity signal between selected pad elements effective to identify a cassette to an interrogation apparatus, such as apparatus 100 in FIG. 1. In such case, a particular test can be initiated simply by inserting a cassette into registration in the interrogation apparatus.

Figure 6:
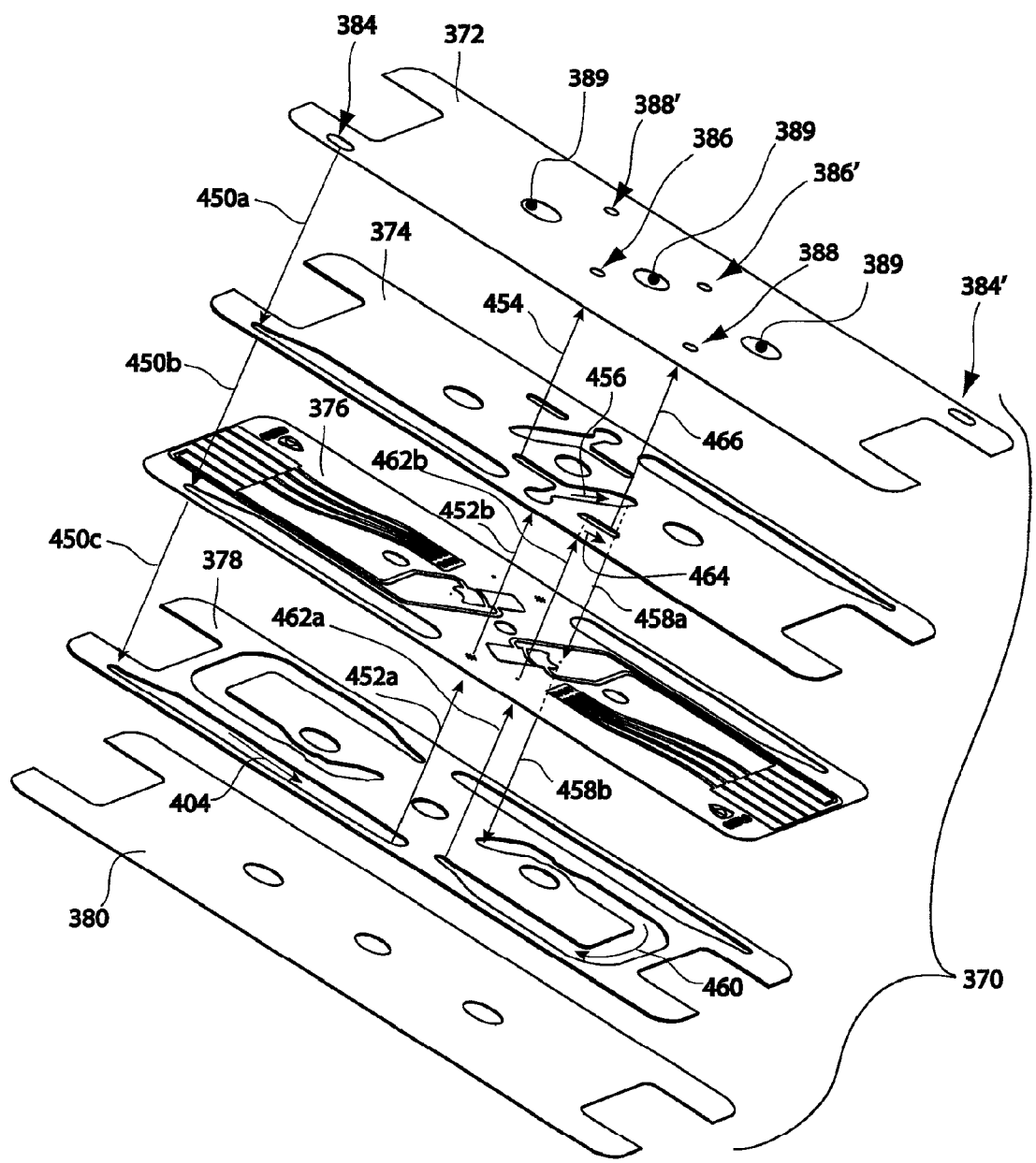
FIG. 6 is an exploded assembly view in perspective of an alternative preferred cassette for use in certain embodiments of the invention.

Elements of a second currently preferred cassette, generally 370, which can be used in accordance with certain principles of the invention, are illustrated with reference to FIGS. 6-10. Cassette 370 is similar to cassette 200, but also includes more structure and additional layers. An exemplary such cassette 370 is also assembled from a plurality of thin film layers that are stacked and bonded together to form a multilayer cassette. With reference to FIG. 6, cassette 370 includes top cap layer 372, top channel layer 374, interrogation layer 376, bottom channel layer 378, and bottom cap layer 380.

The currently preferred top cap layer 372 and bottom cap layer 380 may be made from 0.005" thick transparent polyester film. Desirably, the cap layers 372, 380, and at least a portion of the interrogation layer 376, are structured to cooperate for operable transmission of radiation (e.g. light 156) through the cassette 370.

Workable channel layers 374 and 378 may be made from 0.010" thick double-sided acrylic based adhesive film stock. In such case, the center carrier layer may be 0.007" thick polyester film with 0.0015" thick adhesive coated on each side. A currently preferred interrogation layer 376 may be made from an assortment of materials, depending upon the intended use for the particular sensor that will be constructed. A clear 0.005" thick polyester film may be used for sensors structured to interrogate impedance alone, or in combination with optically-based interrogation. It is preferred to employ an opaque polyamide film for sensors structured to interrogate impedance and fluorescence (or just fluorescence). When present, an opaque film layer inherently resists transmission of undesired radiation toward a Stokes' shift detection sensor (not illustrated, but which can be included in an interrogation apparatus 100).

Similar to cassette 200, the illustrated cassette 370 is a two-ended arrangement structured to provide duplicated structure forming first and second sensors on the same removable and reversible cassette 370. For clarity, the duplicated structures included in the illustrated second sensor and designated by numeral are again indicated with a prime. The illustrated arrangement permits associating the cassette 370 at a first orientation with an interrogation apparatus, running a first test, then removing and reversing the cassette 370 to interface with the interrogation device at a second orientation to perform a second test. The first and second tests may be the same type of test, or different tests, performed on different fluid samples. It is within contemplation that the first and second tests may not be the same, and may also be performed on at least a portion of the same fluid sample. For example, fluid may be passed through one sensor arrangement to a common storage chamber before being passed through a second, or subsequent, sensor arrangement on a single alternatively structured cassette. It is within contemplation to provide a multi-ended arrangement providing a further increased number of sensors (e.g. 3, or 4, or more) on the same cassette, or cartridge. A single-ended cassette is also within contemplation.

With continued reference to FIG. 6, top cap layer 372 provides a sample loading port 384, a vent 386, and a vacuum application port 388. A plurality of over-size alignments holes 389 are also included. Alignment holes 389 are over-sized to provide clearance for other precise alignment structure during assembly of the cartridge 370. Alternative precision alignment structure may be provided for certain layers, such as 372, 374, 378 and 380, and can enforce consistent orientation of a cassette with respect to an interrogation apparatus. Certain alignment structure used primarily for assembly may be redacted from the finished cassette during a manufacturing step. Also, in certain embodiments, vent ports 386 are not included.

Figure 7:
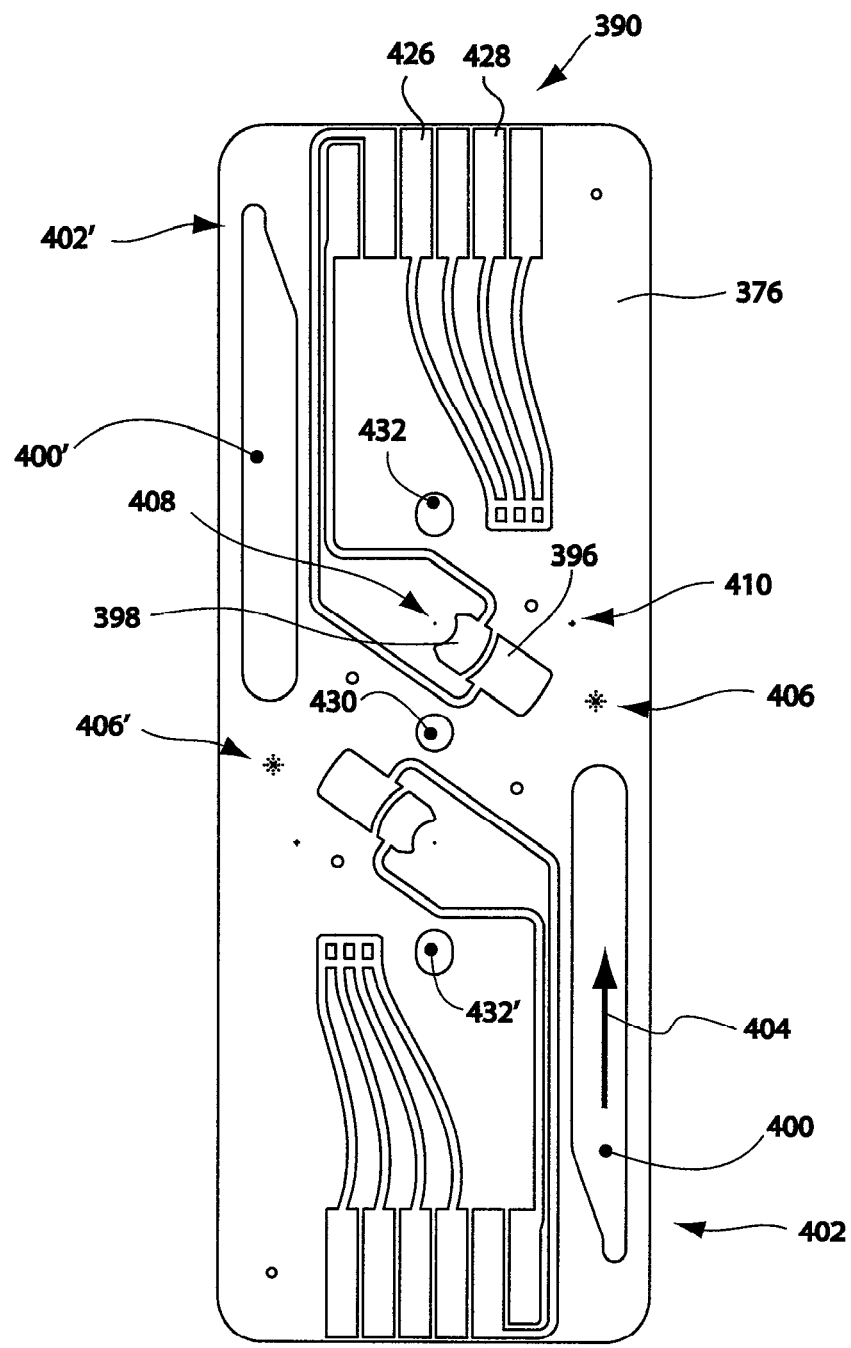
FIG. 7 is a top plan view of an interrogation layer of the cassette in FIG. 6.

With reference now to FIG. 7, interrogation layer 376 carries a plurality of surface contact electrical pads, generally indicated at 390. While alternative deposition of conductive material is operable, it is currently preferred to print the contact pads 390 and other electrically conductive traces and structures using electrically conductive ink and a web-based screen printing process that lends itself to mass production.

As illustrated in FIG. 7, interrogation layer 376 carries a first driving electrode 396 and a first detection electrode 398. A plurality of apertures and channels are removed from the film forming interrogation layer 376. As illustrated, a partial length channel 400 is disposed to receive a fluid sample for interrogation. The sample is typically loaded at proximal end 402, and flows in the direction indicated by arrow 404, toward debris filter 406. An exemplary debris filter resists passage of undesired particulate matter toward the interrogation aperture 408. It is currently preferred to laser drill a plurality of small apertures in combination to form a sort of screen-like debris filter 406. An additional aperture structure includes fluid exit vent 410. Desirably, exit vent 410 is structured to permit application of vacuum to cause fluid flow through passages in the cartridge 370, and to apply capillary attraction to resist flow of fluid beyond the vent 410, itself.

Figure 8:
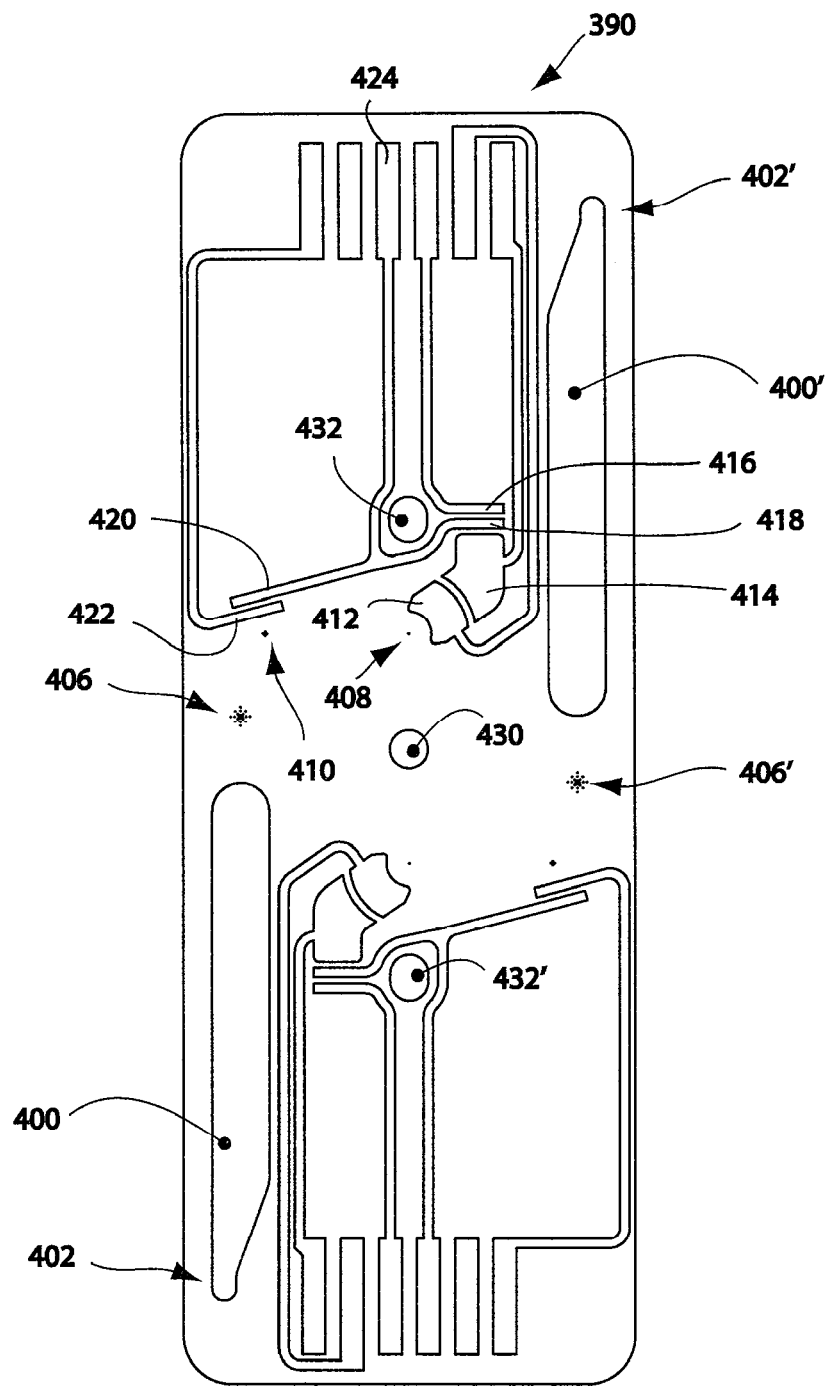
FIG. 8 is a bottom plan view of the interrogation layer in FIG. 7.

With particular reference to FIG. 8, the other side of interrogation layer 376 includes additional electrical contact pads, generally 390. In the illustrated embodiment, the electrical contact pads 390 disposed on one side are not disposed in electrical communication with electrical contact pads 390 on the other side, although such may be convenient in certain cases. Electrically conductive traces extending from the contact pads are configured to provide a second interrogation electrode 412 and a second driving electrode 414.

Still with reference to FIG. 8, a first trigger electrode 416 and a second trigger electrode 418 are disposed down stream of second detection electrode 412 and second driving electrode 414 and may therefore detect a fluid flow arrival boundary. Such an arrangement permits trigger electrode 416 and trigger electrode 418 to operate as an electrically-based trigger that is inherently tripped by a fluid flow boundary, and can be used to begin data collection during the test of a fluid sample.

A third trigger electrode 420 and a fourth trigger electrode 422 are also illustrated in FIG. 8 as being disposed down stream of second detection electrode 412 and second driving electrode 414 and may therefore cooperate to detect a fluid flow arrival boundary at a second location. This first trigger is disposed near the vent aperture 410. Such an arrangement permits electrode 420 and 422 to operate as an electrically-based trigger that can be used to detect the "end of test" for a fluid sample when using the known volume method with respect to the volume in channel 442 and disposed between trigger or boundary detection locations.

For convenience, electrode surface contact pad 424 is in electrical communication with both of electrode 418 and 420, and can therefore be used to apply a common reference signal, such as ground. On the other side of layer 376, electrical contact pads including 426 and 428 are in electrical communication through a multi-branch arrangement. Branches may be severed during manufacture of a cassette and the resulting continuity between the pads may be used for several purposes. For non-limiting examples: in a continuity check to verify proper insertion of a sensor into engagement in a preferred interrogation device, and to identify a cassette as a certain type. It should be noted that certain sensors may be constructed having a different number of driving, detecting, verification, and/or trigger electrodes, or even none.

Illustrated layer 376 also includes a plurality of alignment apertures. Alignment aperture 430 is common to alignment structure used for both ends of the cartridge 370, and imposes an X-Y location at a known reference spot on the cartridge 370 with respect to a currently preferred interrogation apparatus. Alignment slot 432 imposes substantially only a rotational orientation of an installed cartridge 370 with respect to that X-Y location. Desirably, one of the apertures 430, 432 is slotted, and the other is not. Such an arrangement is effective to provide a complete rigid body constraint in a plane, and helps to avoid binding of the cassette during its installation into, or removal from, an interrogation device. The radius of illustrated round alignment aperture 430 is 0.050". The distance between the radii of alignment slot 432 is 0.025" and the radii are 0.050". Cooperating alignment pins in the preferred interrogation device have diameters of 0.1000", and the alignment pins of the preferred interrogation device are precision ground to a tolerance of ±0.0001". Planar orientation of the cartridge is typically enforced by other clamping structure associated with the preferred interrogation device.

Figure 9:
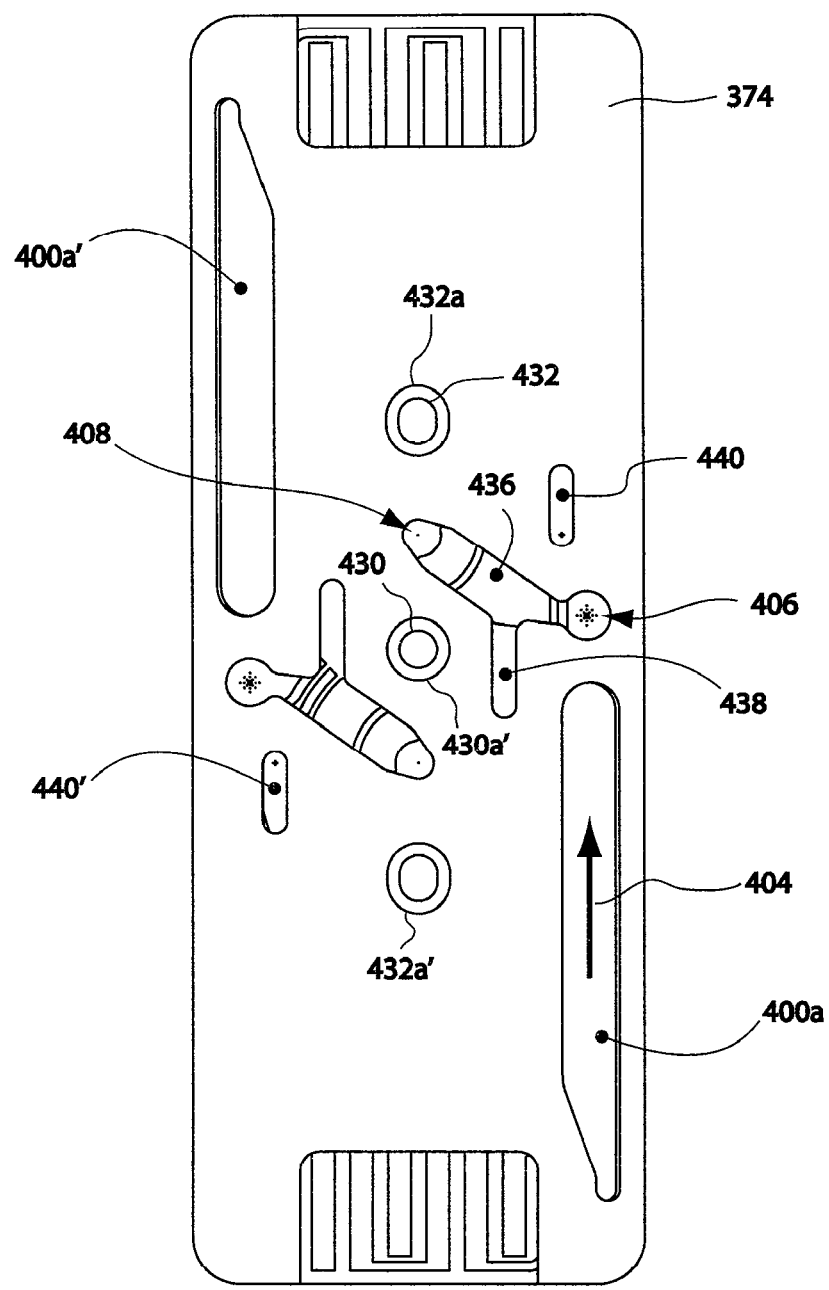
FIG. 9 is a top plan view of a partially assembled portion of the cassette in FIG. 6.

With reference now to FIG. 9, top channel layer 374 includes a plurality of channel structures. Partial-length fluid receiving channel 400a cooperates with channel 400 in layer 376 to permit introduced sample fluid to flow in the direction indicated by arrow 404. Bridge channel 436 transports fluid from debris filter 406 toward interrogation aperture 408. An optional dogleg channel portion 438 may communicate to an optional vent 386 (see FIG. 6) at the top of the cartridge 370, and facilitates loading a fluid sample into the cartridge 370. Buffer channel 440 communicates from exit vent 410 toward a vacuum port 388 (see FIG. 6) on top of the cartridge 370. Along with over-size apertures 389, alignment apertures 430a and 432a are also desirably pulled back during a manufacture step to avoid causing a potential structural interference with respect to alignment apertures 430 and 432 disposed in penetration though the interrogation layer.

Figure 10:
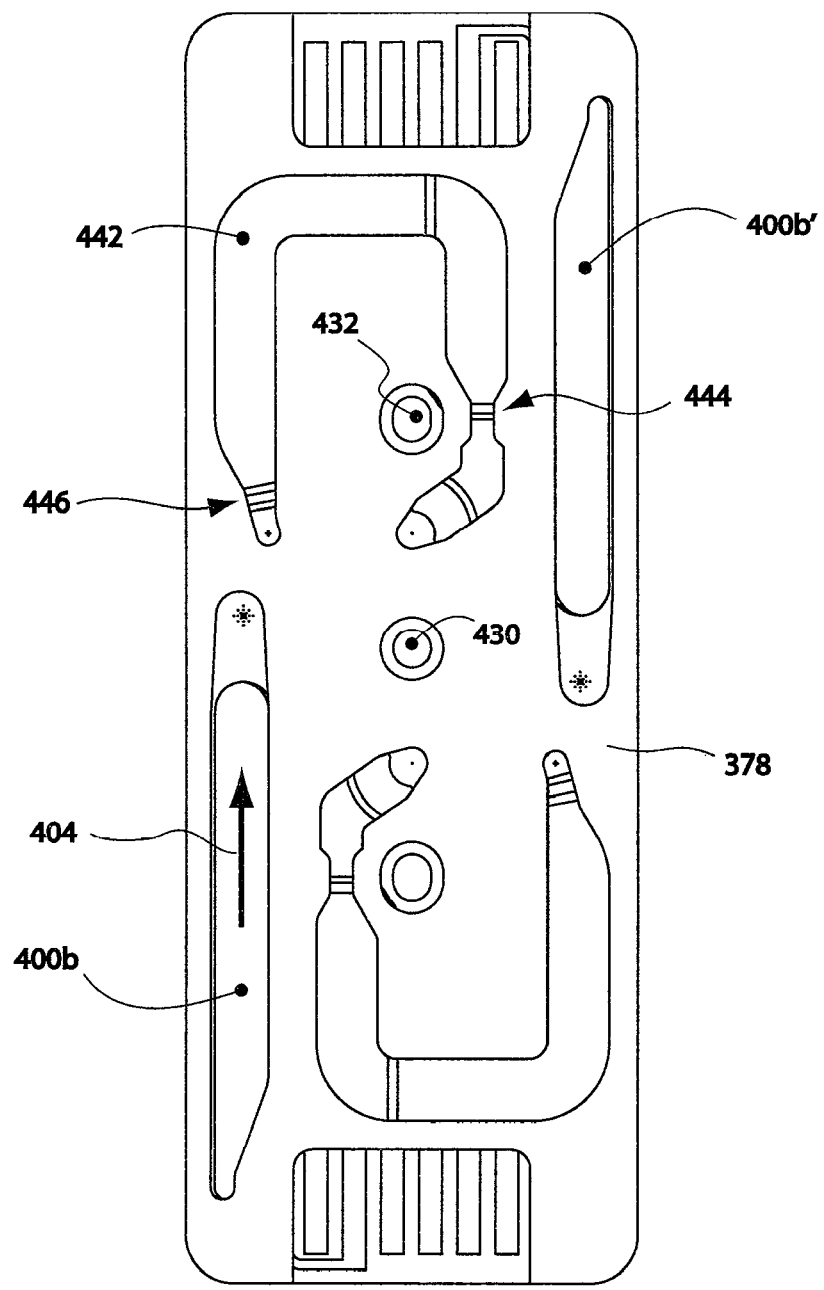
FIG. 10 is a bottom plan view of a partially assembled portion of the cassette in FIG. 6.

With reference now to FIG. 10, bottom channel layer 378 carries full-length sample receiving channel 400b. Channel 400b communicates introduced fluid underneath layer 376 to the bottom of debris filter 406. Channel 442 receive fluid downstream of interrogation aperture 408. In certain embodiments, a first electrically-based trigger, generally indicated at 444, is disposed near one end of the chamber formed by channel 442. A workable trigger may be formed between two dedicated electrodes, or sometimes between one dedicated electrode and a shared electrode. Sometimes, it is desirable for paired cooperating trigger electrodes (sometimes also called test electrodes) to be narrow and disposed as close together as possible. An electrode area can be fairly small (e.g. 0.025"×0.065") and the current printing process can easily maintain a 0.015" spacing between printed electrodes.

Illustrated trigger 444 in FIG. 10 is formed between electrodes 414 and 418 (see FIG. 8). A trigger at a location such as trigger 444 is operable as a "start" trigger, to begin collection of data during an interrogation of a fluid sample. It has been determined that a single impedance-detecting electrode, such as 418, cooperating with a source or driving electrode 414 is more reliable than a cooperating dedicated pair of electrodes 418, 416 disposed in very close association with a driving electrode such as 414.

A second electrically-based trigger, generally 446, may be disposed spaced apart from trigger 444 by a known volume provided by channel 442. Illustrated trigger 446 is formed by electrodes 420 and 422 (see FIG. 8). In certain cases, a second known volume may be defined by channel and aperture structure disposed between trigger 444 and an upstream trigger, such as may be formed between electrodes 292 and 294 (see FIG. 7).

Known volumetric trigger spacing and collection of data signals including a common time component or base, permit: starting and stopping test data collection; control for application of vacuum; confirmation of processing a desired sample volume; and calculation of volumetric rate of processing, among other capabilities.

With reference again to FIG. 6, the fluid flow path through cassette 370 will now be described. In one type of test, a sample is typically introduced to sample loading port 384 using a pipette instrument to accurately dispense a desired test volume, or sometimes a surplus volume. Entering fluid flow is represented by arrows 450a, 450b and 450c. Sample fluid then flows along a channel formed by channel portions 400, 400a, and 400b in the direction indicated by arrow 404. As indicated by arrows 452a and 452b, fluid flow through debris filter 406 to channel 436. Air may be passed out aperture 386, as indicated by arrow 454. During a test, fluid flows along channel 436 in the direction indicated by arrow 456. Fluid then flows through interrogation aperture 408 as indicated by partially hidden arrows 458a and 458b. Fluid flow in channel 442 is indicated by arrow 460. Fluid then flows through vent 410 as indicated by arrows 462a and 462b. Fluid then flows along channel 440 in layer 374, in the direction indicated by arrow 464, before potentially exiting vacuum port 388, indicated by arrow 466. In certain cases, channel 440 may provide a buffer to resist escape of fluid from a cartridge 370.

Typically, an Excimer laser is used to form the interrogation apertures 408 and alignment apertures 430 and 432. A DPSS laser is generally used to form all of the other channel and aperture structure (filters, vents, channels, etc.). The excimer can cut the currently preferred 44 µm diameter interrogation aperture 408 within ±2 microns. Repeatability of the DPSS is more like plus/minus 5 microns. The large alignment holes 430, 432 are manufactured (laser cut) with extreme precision relative to the laser drilled interrogation aperture 108. Use of the more accurate laser allows the interrogation aperture 408 to be mechanically aligned, from cassette to cassette, to the laser beam of a cooperating docking station of a preferred interrogation device with an accuracy of about 20 µm to 50 µm. Here, "accuracy" means that the center of the aperture is disposed within a repeatable "accuracy" radius of the theoretical centerline of an interrogation location provided by a cooperatingly structured interrogation device.

Figure 11:
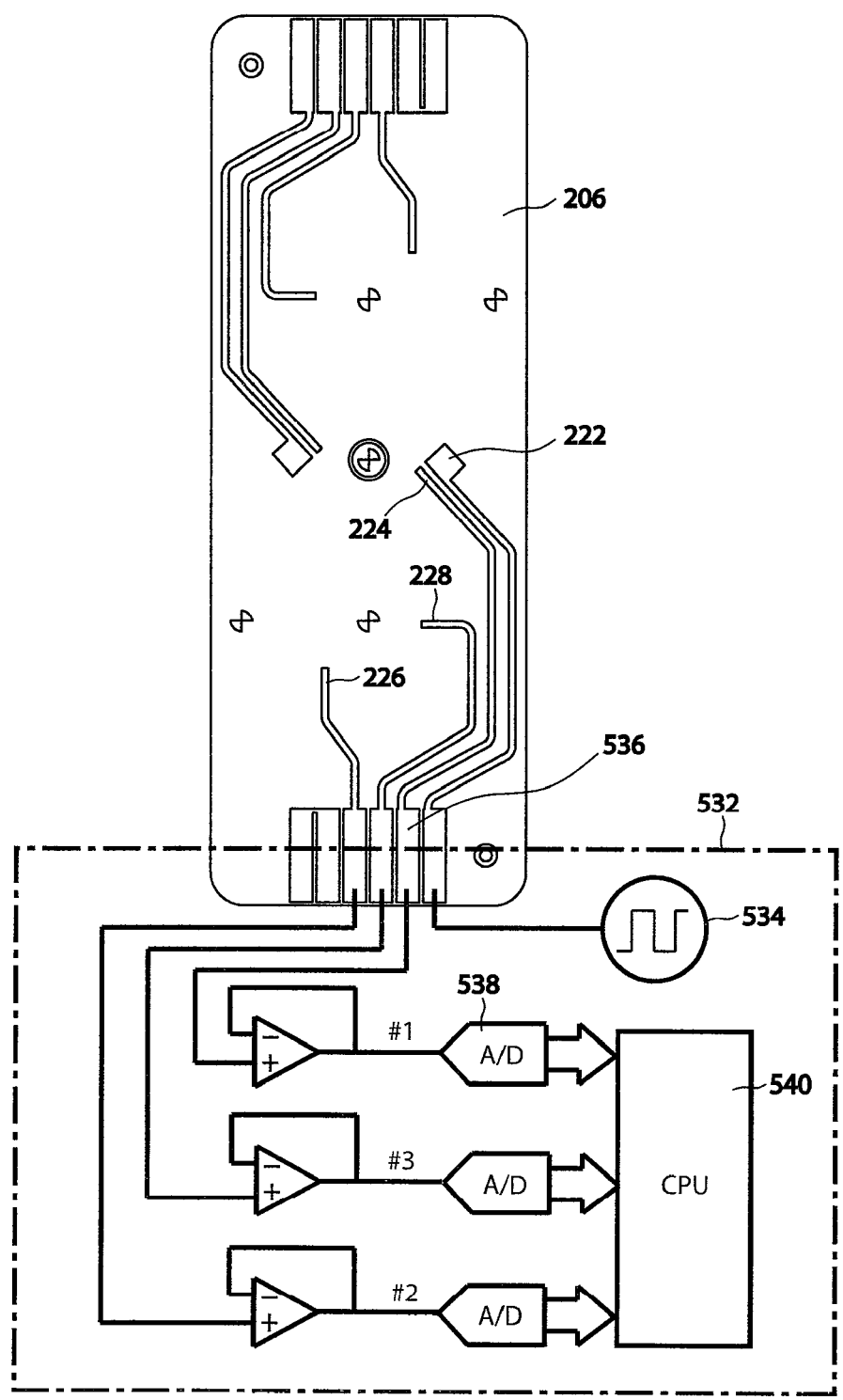
FIG. 11 is a plan view of a portion of the cassette in FIG. 5 interfacing with a schematic representative of an interrogation apparatus.

FIG. 11 illustrates a cassette structured for electrical fluid position detection and optically-based particle interrogation interfacing with electrically-based interrogation structure of an interrogation apparatus, such as apparatus 100. The electrical interrogation structure indicated by dashed box 532 is desirably included in structure provided by an apparatus 100. An edge connector 219 (see FIG. 4) can conveniently couple a cassette to the apparatus 100. One or more electrical signal may be applied to one or more contact pad to provide a stimulus signal to sample fluid in the cassette. A workable signal includes a 50 kHz, square-wave, 30 mV p-p oscillating electrical signal, e.g. such as might be applied by signal generator 534.

An electrical signal may be monitored with respect to ground at an electrode (e.g. at contact pad 536 for electrode 224) to determine fluid behavior inside the cassette 200. When the circuit monitored at pad 536 is no longer open, the fluid boundary has at least reached electrode 224. An uninterrupted match to the applied signal as fluid continues to flow will indicate lack of bubbles in the sample fluid. The leading edge of the fluid boundary will be determined by successive closed circuits formed by the electrolytic fluid contacting electrodes 226 and 228. Signals may be converted by an A/D converter 538, and passed to the computer processing unit 540. Optically-based data may be obtained (using structure such as illustrated in FIG. 4 and previously described) at selected instances in time that may be triggered, for example, by one or more monitored signal, or periodically.

Figure 12:
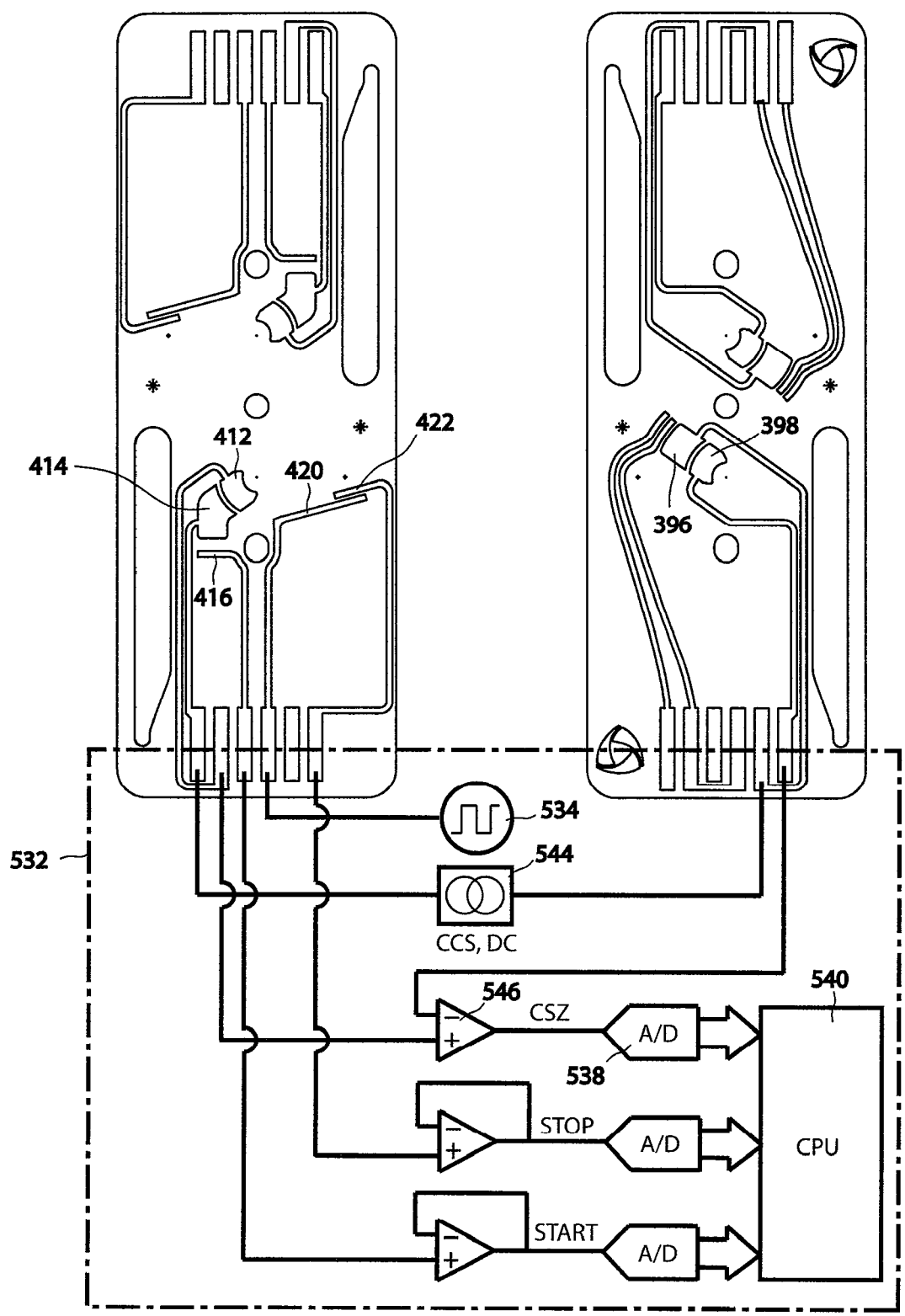
FIG. 12 is a plan view of an alternative interrogation portion, of a cassette similar to that illustrated in FIGS. 6-10, interfacing with a schematic representative of an interrogation apparatus.

Electrical interrogation structure 532 illustrated in FIG. 12 is only a partial schematic to illustrate selected operation desired between an exemplary cassette 370 and an interrogation apparatus 100. Note: only the interrogation layer of a single cassette 370 is illustrated, but showing both sides simultaneously.

A start trigger signal potential may be created by application of a time-varying signal from signal generator 544 to the contact pad that communicates to electrode 414. A signal is monitored at the contact pad that communicates with trigger electrode 416. When a signal (e.g. not open-circuit) is first detected at electrode 416, the fluid sample has wet-out the driven electrode 414, and the fluid front boundary is at the location of electrode 416, so collection of test data may be started responsive to that detection of that signal. The central processing unit 540 can be variously programmed to cause multiple responses to different inputs, such as to: start and/or stop a test, cause data collection, apply a reduced pressure profile to a cassette, maintain a desired vacuum, plot data, and even discriminate between installed cassettes to run a test corresponding to the particular cassette type, and the like.

A stop trigger signal potential may be created by application of a signal from signal generator 534 to the contact pad that communicates to electrode 420. A signal is monitored at the contact pad that communicates with trigger electrode 422. When a signal (e.g. not open-circuit) is first detected at electrode 422, the fluid sample has wet-out the driven electrode 420, and the fluid front boundary is at the location of electrode 422. The signal is passed to CPU 540, and the data collection and reduced pressure can be stopped in accordance with programmed behavior of interrogation apparatus 100. Generally, it is desirable to terminate at least the applied vacuum before the sample fluid is drawn significantly beyond the stop trigger and escapes from the cassette 370.

To detect particles in an interrogation zone according to a preferred variation of the Coulter effect in the structure illustrated in FIG. 12, a Direct Current, constant current source signal is applied by signal generator 544 between a contact pad communicating with driving electrode 414 and the contact pad communicating with driving electrode 396. A workable arrangement includes applying +15 Volt at one contact pad, and −15 Volts at the other contact pad. Voltage change responsive to particle travel through an orifice is monitored between detection electrodes 412 and 398. The monitored differential signal is transmitted by an operational amplifier 546 and converted to digital format by an A/D converter 538, then passed to the CPU 540 for further processing.

Figure 13:
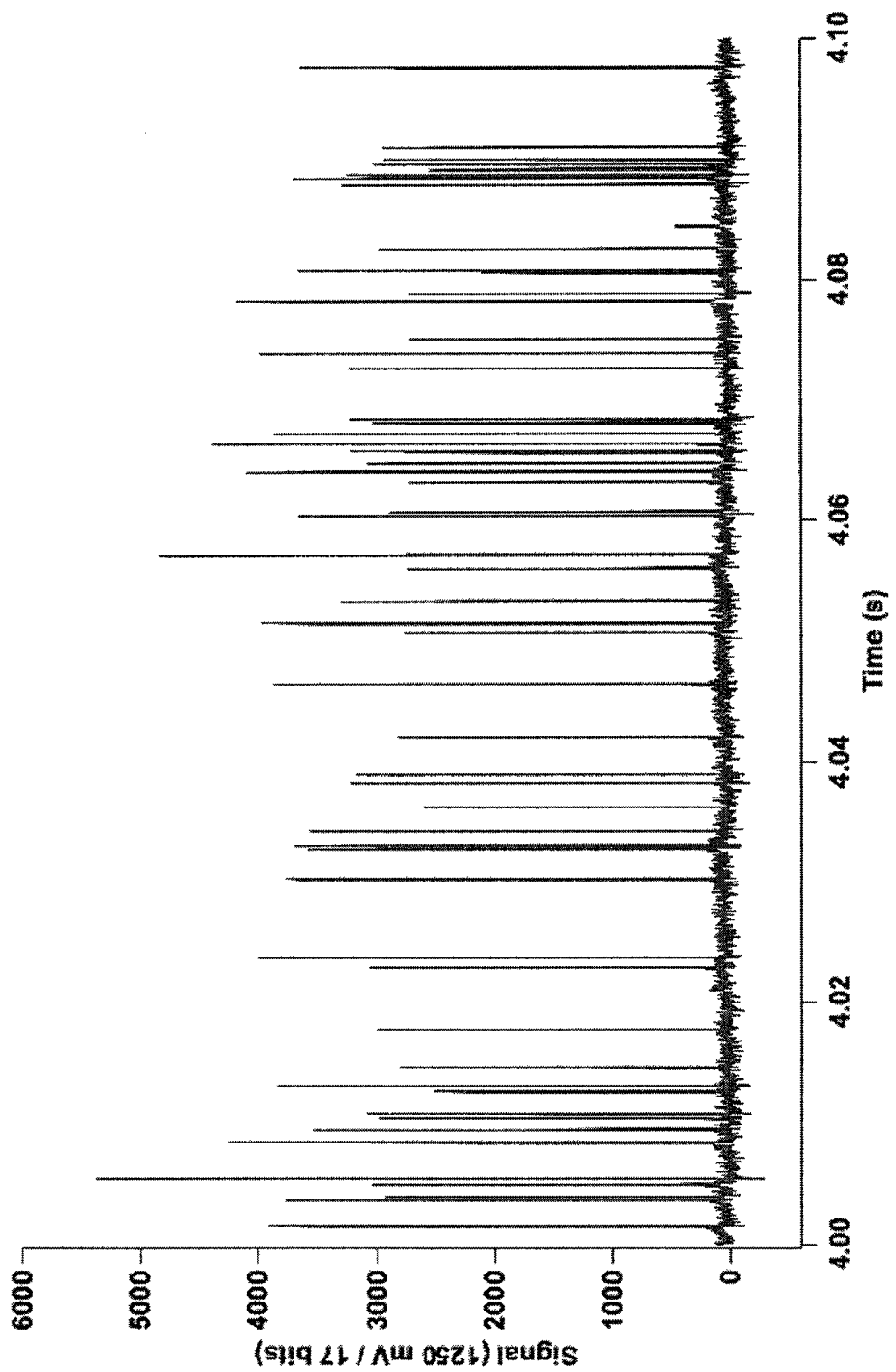
FIG. 13 is an X-Y plot of raw impedance data showing a measured Coulter effect.
Figure 14:
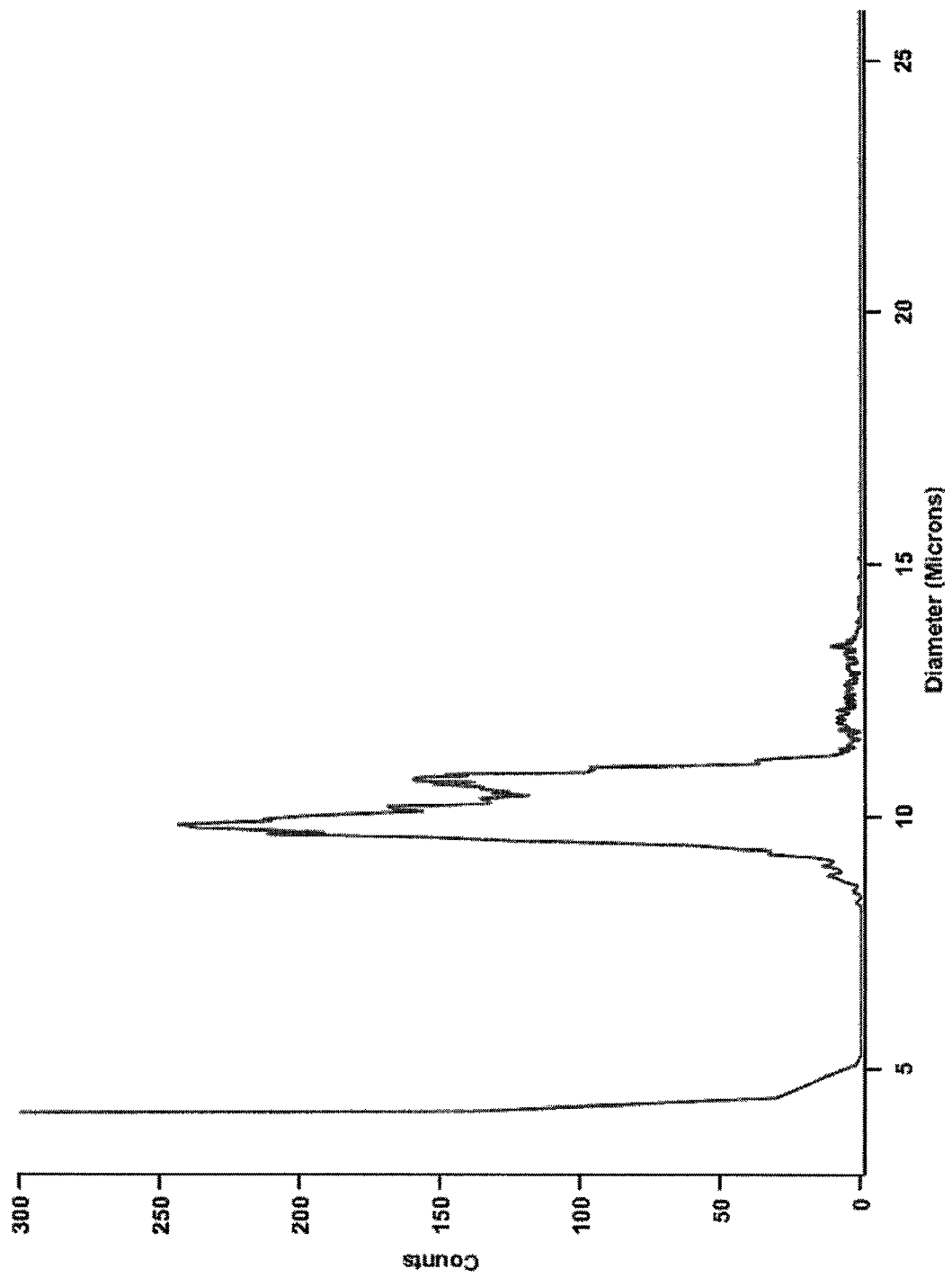
FIG. 14 is a histogram plot of particle size range that has been extracted from data such as set forth in FIG. 13.

An exemplary raw data monitored impedance signal is set forth in FIG. 13. A corresponding histogram reflecting particle size distribution in a sample having particles that are nominally 10 microns in size is set forth in FIG. 14. The sharp rising line on the left side of the plot in FIG. 14 represents the threshold of the electrical baseline noise. A histogram having a larger range in particle size for each defined sub-size, or group, would have more distinct bars, rather than approximating an X-Y line plot, as illustrated. A currently preferred histogram includes 1200 discrete bin sizes. The number of particles within each sub-size are included in the count for each bin.

While the invention has been described in particular with reference to certain illustrated embodiments, such is not intended to limit the scope of the invention. The present invention may be embodied in other specific forms without departing from its spirit or essential characteristics. The described embodiments are to be considered as illustrative and not restrictive. The scope of the invention is, therefore, indicated by the appended claims rather than by the foregoing description. All changes which come within the meaning and range of equivalency of the claims are to be embraced within their scope.

What is claimed is:

1. An interrogation apparatus, comprising:
structure configured and arranged to interact with a removable microfluidic cassette to obtain an optically-based signal related to optical particle characterization of a plurality of particles carried by a fluid that can be urged to move through a channel in said cassette, said optically-based signal being extracted from a optical-interrogation location disposed along said channel;
structure configured and arranged to interact with said removable cassette to obtain an electrically-based signal related to at least one of:
identification of said cassette;
a location of a fluid boundary that can be urged to move through said channel in said cassette; or
characterization of one or more particles carried by said fluid; and
a display element on which a result from processing one or more of said optically-based signal and said electrically-based signal may be shown;
said cassette comprising:
a cap layer disposed to form a fluid-resistant cover on one side of a channel segment, at least a portion of said cap layer being substantially transparent in a through-the-thickness direction;
a sample-receiving orifice disposed in fluid communication with said channel segment;
a vent disposed in fluid communication with said channel segment at a location disposed downstream of said sample-receiving orifice; and
an interrogation layer disposed to form a fluid-resistant cover on the other side of said channel segment, at least a portion of said interrogation layer being substantially transparent in a through-the-thickness direction, wherein:
said interrogation layer carries a plurality of surface electrodes disposed to contact fluid carried inside a channel comprising said channel segment; and
a portion of said cap layer, said channel, and said interrogation layer cooperate to form a substantially transparent window through the thickness of said cassette at said optical-interrogation location.

2. The apparatus according to claim 1, wherein:
said optically-based signal is related to particle viability characterization.

3. The apparatus according to claim 1, wherein:
said apparatus is configured in harmony with said cassette to permit acquisition of data to determine location of a fluid boundary at a plurality of locations spaced apart along said channel.

4. The apparatus according to claim 1, wherein:
at least a portion of said channel is formed in said cap layer.

5. The apparatus according to claim 1, wherein:
a portion of said channel is formed as a through-the-thickness cut-out from a channel layer.

6. The apparatus according to claim 1, wherein:
said cassette further comprises:
an interrogation aperture disposed in said channel, said interrogation aperture being structured to urge particles carried in sample fluid into substantially single-file travel there-through; and
electrode structure configured and arranged to permit detection of an electrically-based signal, by said interrogation apparatus, effective to characterize said particles in accordance with the Coulter principle.

7. The apparatus according to claim 1, wherein:
said apparatus further comprises:
a vacuum source structured to couple with a vent of said cassette to permit urging fluid flow through a channel in said cassette;
a plurality of electrical contacts structured to interface with electrical contact pads of said cassette;
said display element being capable of visually indicating a bar chart; and
a processor arranged to manipulate at least one of said optically-based signal and said electrically-based signal, and to output corresponding information to said display element.

8. A method, comprising:
providing an interrogation apparatus structured according to claim 1;
loading a cooperating removable microfluidic cassette into operable registration with respect to said interrogation apparatus;
urging flow of a sample fluid through a channel disposed inside said cassette until a first electrically-based signal related to a first fluid boundary location in said channel is generated; and
obtaining a first optically-based signal to permit determination of a first volumetric particle count related to said sample fluid.

9. The method according to claim 8, wherein:
said first optically-based signal is obtained while a portion of said sample fluid is stationary in said channel.

10. The method according to claim 8, wherein:
said first optically-based signal is obtained while a portion of said sample fluid is flowing in said channel.

11. The method according to claim 8, wherein:
said interrogation apparatus is structured in harmony with said cassette such that the step of loading said cassette is effective to identify said cassette to said interrogation apparatus and a corresponding first test sequence is automatically initiated by said interrogation apparatus.

12. The method according to claim 11, wherein:
said corresponding first test sequence comprises application of a sub-atmospheric pressure by said interrogation apparatus to a vent of said cassette.

13. The method according to claim 12, wherein:
subsequent to the step of application of a sub-atmospheric pressure by said interrogation apparatus to a vent of said cassette, a user installs a quantity of fluid into said cassette, and initiates a second test sequence.

14. The method according to claim 13, wherein:
said second test sequence comprises obtaining said first optically-based signal to permit determination of said first volumetric particle count.

15. The method according to claim 8 wherein:
obtaining said first optically-based signal comprises:
capturing a first digital image of an area portion of said channel by an image sensor; and processing of digital image data, corresponding to said first digital image and received from said image sensor, in a first algorithm by said interrogation apparatus to determine a volumetric cell count corresponding to said first digital image and volumetric parameters of said optical-interrogation location.

16. The method according to claim 15, wherein:
obtaining said first optically-based signal further comprises:
an autofocuss process initiated by said interrogation apparatus and including feedback from said image sensor.

17. The method according to claim 15, further comprising:
adding a viability dye to said sample fluid prior to interrogation of said sample fluid by said interrogation apparatus;
processing of digital image data received from said image sensor in a second algorithm by said interrogation apparatus to determine a live/dead cell ratio corresponding to said digital image and volumetric parameters of said optical-interrogation location; and
causing information including at least one of: volumetric cell count; viability percentage; and a particle size histogram; to be displayed on said display element.

18. The method according to claim 15, further comprising:
urging flow of said sample fluid through said channel until a second electrically-based signal related to a second fluid boundary location in said channel is detected; and
capturing a second digital image of an area portion of said channel by said image sensor; and
processing of digital image data, corresponding to said second digital image and received from said image sensor, in a first algorithm by said interrogation apparatus to determine a volumetric cell count corresponding to said second digital image and volumetric parameters of said optical-interrogation location; and
causing information including at least one of: volumetric cell count; viability percentage; and a particle size histogram; to be displayed on said display element.

19. The method according to claim 8, further comprising:
urging flow of said sample fluid through an interrogation aperture disposed in said channel, said interrogation aperture being structured to urge particles carried in said sample fluid into substantially single-file travel therethrough; and
obtaining a second electrically-based signal effective to permit characterization of said particles in accordance with the Coulter principle; and
causing information including at least one of: volumetric cell count; viability percentage; and a particle size histogram; to be displayed on said display element.

* * * * *